United States Patent
Dripps et al.

(10) Patent No.: US 10,376,157 B2
(45) Date of Patent: *Aug. 13, 2019

(54) SYSTEMS AND METHODS FOR DETERMINING RESPIRATION INFORMATION USING PHASE LOCKED LOOP

(71) Applicant: Nellcor Puritan Bennett Ireland, Mervue, Galway (IE)

(72) Inventors: James Dripps, West Linton (GB); James Ochs, Palo Alto, CA (US); Paul S. Addison, Edinburgh (GB)

(73) Assignee: NELLCOR PURITAN BENNETT IRELAND, Mervue, Galway (IE)

( * ) Notice: Subject to any disclaimer, the term of this patent is extended or adjusted under 35 U.S.C. 154(b) by 763 days.

This patent is subject to a terminal disclaimer.

(21) Appl. No.: 15/003,761

(22) Filed: Jan. 21, 2016

(65) Prior Publication Data
US 2016/0135691 A1 May 19, 2016

Related U.S. Application Data

(63) Continuation of application No. 13/343,389, filed on Jan. 4, 2012, now Pat. No. 9,247,896.

(51) Int. Cl.
*A61B 5/0205* (2006.01)
*A61B 5/08* (2006.01)
(Continued)

(52) U.S. Cl.
CPC .......... *A61B 5/0205* (2013.01); *A61B 5/0295* (2013.01); *A61B 5/08* (2013.01);
(Continued)

(58) Field of Classification Search
CPC .... A61B 5/0261; A61B 5/0295; A61B 5/0816
See application file for complete search history.

(56) References Cited

U.S. PATENT DOCUMENTS 3,846,704 A 11/1974 Bessette
4,063,551 A * 12/1977 Sweeney ............ A61B 5/02416
600/479
(Continued)

FOREIGN PATENT DOCUMENTS

EP 0072601 A1 2/1983
EP 1344488 A2 9/2004
(Continued)

OTHER PUBLICATIONS

Long, S. "Phase Locked Loop Circuits." Apr. 27, 2005. https://web.archive.org/web/20081201083334/http://www.ece.ucsb.edu/~long/ece594a/PLL_intro594a_s05.pdf.
(Continued)

*Primary Examiner* — Meredith Weare
(74) *Attorney, Agent, or Firm* — Cantor Colburn LLP (57) ABSTRACT

A patient monitoring system may receive a physiological signal such as a photoplethysmograph (PPG) signal that exhibits frequency and amplitude modulation based on respiration. A phase locked loop may generate a frequency demodulated signal and an amplitude demodulated signal from the PPG signal. An autocorrelation sequence may be generated for each of the frequency demodulated signal and the amplitude demodulated signal. The autocorrelation sequences may be combined and respiration information may be determined based on the combined autocorrelation sequence.

20 Claims, 5 Drawing Sheets

(51) Int. Cl.
*A61B 5/0295* (2006.01)
*A61B 5/00* (2006.01)
*A61B 5/1455* (2006.01)

(52) U.S. Cl.
CPC ........ *A61B 5/0816* (2013.01); *A61B 5/14551* (2013.01); *A61B 5/7225* (2013.01); *A61B 5/7246* (2013.01); *A61B 5/7278* (2013.01); *A61B 5/742* (2013.01)

(56) References Cited

U.S. PATENT DOCUMENTS

| | | | |
|---|---|---|---|
| 4,458,518 A | 7/1984 | Ingle | |
| 4,916,403 A * | 4/1990 | Sudoh | H03L 7/0992 327/114 |
| 4,958,638 A | 9/1990 | Sharpe et al. | |
| 5,188,108 A | 2/1993 | Secker | |
| 5,285,783 A | 2/1994 | Secker | |
| 5,285,784 A | 2/1994 | Secker | |
| 5,368,026 A | 11/1994 | Swedlow et al. | |
| 5,398,682 A | 3/1995 | Lynn | |
| 5,558,096 A | 9/1996 | Palatnik | |
| 5,584,295 A | 12/1996 | Muller et al. | |
| 5,588,425 A | 12/1996 | Sackner et al. | |
| 5,595,176 A | 1/1997 | Yamaura | |
| 5,605,151 A | 2/1997 | Lynn | |
| 5,862,805 A | 1/1999 | Nitzan | |
| 5,865,736 A | 2/1999 | Baker, Jr. et al. | |
| 5,891,023 A | 4/1999 | Lynn | |
| 6,002,952 A | 12/1999 | Diab et al. | |
| 6,035,223 A | 3/2000 | Baker | |
| 6,081,742 A | 6/2000 | Amano et al. | |
| 6,095,984 A | 8/2000 | Amano et al. | |
| 6,129,675 A | 10/2000 | Jay | |
| 6,135,966 A | 10/2000 | Ko | |
| 6,178,261 B1 | 1/2001 | Williams et al. | |
| 6,223,064 B1 | 4/2001 | Lynn | |
| 6,229,856 B1 | 5/2001 | Diab et al. | |
| 6,238,351 B1 | 5/2001 | Orr et al. | |
| 6,325,761 B1 | 12/2001 | Jay | |
| 6,334,065 B1 | 12/2001 | Al-Ali et al. | |
| 6,342,039 B1 | 1/2002 | Lynn et al. | |
| 6,350,242 B1 | 2/2002 | Doten et al. | |
| 6,405,076 B1 | 6/2002 | Taylor et al. | |
| 6,449,501 B1 | 9/2002 | Reuss | |
| 6,463,311 B1 | 10/2002 | Diab | |
| 6,506,153 B1 | 1/2003 | Littek et al. | |
| 6,561,986 B2 | 5/2003 | Baura et al. | |
| 6,564,077 B2 | 5/2003 | Mortara | |
| 6,606,511 B1 | 8/2003 | Ali et al. | |
| 6,609,016 B1 | 8/2003 | Lynn | |
| 6,684,090 B2 | 1/2004 | Ali et al. | |
| 6,694,178 B1 | 2/2004 | Soula et al. | |
| 6,702,752 B2 | 3/2004 | Dekker | |
| 6,709,402 B2 | 3/2004 | Dekker | |
| 6,748,252 B2 | 6/2004 | Lynn et al. | |
| 6,754,516 B2 | 6/2004 | Mannheimer | |
| 6,760,608 B2 | 7/2004 | Lynn | |
| 6,783,498 B2 | 8/2004 | Sackner et al. | |
| 6,816,741 B2 | 11/2004 | Diab | |
| 6,839,581 B1 | 1/2005 | El Solh et al. | |
| 6,896,661 B2 | 5/2005 | Dekker | |
| 6,905,470 B2 | 6/2005 | Lee et al. | |
| 6,925,324 B2 | 8/2005 | Shusterman | |
| 6,931,269 B2 | 8/2005 | Terry | |
| 6,966,878 B2 | 11/2005 | Schoisswohl et al. | |
| 6,970,792 B1 | 11/2005 | Diab | |
| 6,980,679 B2 | 12/2005 | Jeung et al. | |
| 7,020,507 B2 | 3/2006 | Scharf et al. | |
| 7,035,679 B2 | 4/2006 | Addison et al. | |
| 7,043,293 B1 | 5/2006 | Baura | |
| 7,044,918 B2 | 5/2006 | Diab | |
| 7,070,566 B2 | 7/2006 | Medero et al. | |
| 7,079,888 B2 | 7/2006 | Oung et al. | |
| 7,147,601 B2 | 12/2006 | Marks et al. | |
| 7,177,682 B2 | 2/2007 | Lovett | |
| 7,190,261 B2 | 3/2007 | Al-Ali | |
| 7,215,986 B2 | 5/2007 | Diab et al. | |
| 7,218,966 B2 | 5/2007 | Haefner | |
| 7,254,425 B2 | 8/2007 | Lowery et al. | |
| 7,283,870 B2 | 10/2007 | Kaiser et al. | |
| 7,336,982 B2 | 2/2008 | Yoo | |
| 7,355,512 B1 | 4/2008 | Al-Ali | |
| 7,367,339 B2 | 5/2008 | Hickle | |
| 7,367,949 B2 | 5/2008 | Korhonen et al. | |
| 7,398,115 B2 | 7/2008 | Lynn | |
| 7,403,806 B2 | 7/2008 | Norris | |
| 7,407,486 B2 | 8/2008 | Huiku et al. | |
| 7,415,297 B2 | 8/2008 | Al-Ali et al. | |
| 7,438,683 B2 | 10/2008 | Al-Ali et al. | |
| 7,440,787 B2 | 10/2008 | Diab | |
| 7,470,235 B2 | 12/2008 | Moriya et al. | |
| 7,485,095 B2 | 2/2009 | Shusterman | |
| 7,496,393 B2 | 2/2009 | Diab et al. | |
| 7,499,835 B2 | 3/2009 | Weber et al. | |
| 7,523,011 B2 | 4/2009 | Akiyama et al. | |
| 7,561,912 B2 | 7/2009 | Schatz et al. | |
| 7,610,324 B2 | 10/2009 | Troyansky et al. | |
| 7,690,378 B1 | 4/2010 | Turcott | |
| 7,801,591 B1 | 9/2010 | Shusterman | |
| 7,869,980 B2 | 1/2011 | Casler et al. | |
| 7,887,502 B2 | 2/2011 | Ross et al. | |
| 7,894,868 B2 | 2/2011 | Al-Ali et al. | |
| 7,899,507 B2 | 3/2011 | Al-Ali et al. | |
| 7,976,472 B2 | 7/2011 | Kiani | |
| 7,988,637 B2 | 8/2011 | Diab | |
| 8,019,400 B2 | 9/2011 | Diab et al. | |
| 8,046,040 B2 | 10/2011 | Ali et al. | |
| 8,130,105 B2 | 3/2012 | Al-Ali et al. | |
| 8,203,438 B2 | 6/2012 | Kiani et al. | |
| 8,275,553 B2 | 9/2012 | Amundson et al. | |
| 8,364,223 B2 | 1/2013 | Al-Ali et al. | |
| 8,755,871 B2 | 6/2014 | Weng et al. | |
| 8,880,576 B2 | 11/2014 | Ochs et al. | |
| 9,247,896 B2 * | 2/2016 | Dripps | A61B 5/0205 |
| 9,307,928 B1 * | 4/2016 | Al-Ali | A61B 5/0816 |
| 2002/0038078 A1 | 3/2002 | Ito | |
| 2002/0117173 A1 | 8/2002 | Lynn et al. | |
| 2003/0036685 A1 | 2/2003 | Goodman | |
| 2003/0158466 A1 | 8/2003 | Lynn | |
| 2003/0163054 A1 | 8/2003 | Dekker | |
| 2004/0015091 A1 | 1/2004 | Greenwald et al. | |
| 2004/0225225 A1 | 11/2004 | Naumov et al. | |
| 2004/0260186 A1 * | 12/2004 | Dekker | A61B 5/0205 600/483 |
| 2005/0004479 A1 | 1/2005 | Townsend et al. | |
| 2005/0022606 A1 | 2/2005 | Partin et al. | |
| 2005/0027205 A1 | 2/2005 | Tarassenko et al. | |
| 2005/0049470 A1 | 3/2005 | Terry | |
| 2005/0070774 A1 | 3/2005 | Addison et al. | |
| 2005/0115561 A1 | 6/2005 | Stahmann et al. | |
| 2005/0222502 A1 | 10/2005 | Cooper | |
| 2005/0222503 A1 | 10/2005 | Dunlop et al. | |
| 2006/0122476 A1 | 6/2006 | VanSlyke | |
| 2006/0192667 A1 | 8/2006 | Al-Ali | |
| 2006/0211930 A1 | 9/2006 | Scharf et al. | |
| 2006/0217614 A1 | 9/2006 | Takala et al. | |
| 2006/0258921 A1 | 11/2006 | Addison et al. | |
| 2007/0004977 A1 | 1/2007 | Norris | |
| 2007/0010723 A1 | 1/2007 | Uetela et al. | |
| 2007/0073120 A1 | 3/2007 | Li et al. | |
| 2007/0073124 A1 | 3/2007 | Li et al. | |
| 2007/0129636 A1 | 6/2007 | Friedman et al. | |
| 2007/0149890 A1 | 6/2007 | Li et al. | |
| 2007/0213619 A1 | 9/2007 | Lindner | |
| 2007/0213621 A1 | 9/2007 | Reisfeld et al. | |
| 2007/0255146 A1 | 11/2007 | Andrews et al. | |
| 2007/0293896 A1 | 12/2007 | Haefner | |
| 2008/0067132 A1 | 3/2008 | Ross et al. | |
| 2008/0077022 A1 | 3/2008 | Baker | |
| 2008/0167540 A1 | 7/2008 | Korhonen et al. | |
| 2008/0200775 A1 | 8/2008 | Lynn | |
| 2008/0249382 A1 | 10/2008 | Oh et al. | |
| 2008/0287815 A1 | 11/2008 | Chon et al. | |

(56) References Cited

U.S. PATENT DOCUMENTS

| | | |
|---|---|---|
| 2009/0163784 A1 | 6/2009 | Sarpeshkar et al. |
| 2009/0247837 A1 | 10/2009 | Ochs et al. |
| 2009/0306487 A1* | 12/2009 | Crowe ............... A61B 5/02433 600/322 |
| 2009/0306524 A1 | 12/2009 | Muhlsteff et al. |
| 2009/0326349 A1 | 12/2009 | McGonigle |
| 2009/0326395 A1 | 12/2009 | Watson |
| 2009/0326831 A1 | 12/2009 | McGonigle et al. |
| 2010/0081897 A1 | 4/2010 | Li et al. |
| 2010/0081899 A1 | 4/2010 | McKenna |
| 2010/0113904 A1 | 5/2010 | Batchelder et al. |
| 2010/0113908 A1 | 5/2010 | Vargas et al. |
| 2010/0113909 A1 | 5/2010 | Batchelder et al. |
| 2010/0174160 A1 | 7/2010 | Chance |
| 2010/0286495 A1 | 11/2010 | McGonigle |
| 2010/0292568 A1 | 11/2010 | Droitcour et al. |
| 2010/0324389 A1 | 12/2010 | Moon et al. |
| 2011/0021892 A1 | 1/2011 | Addison et al. |
| 2011/0066062 A1 | 3/2011 | Banet et al. |
| 2011/0071406 A1 | 3/2011 | Addison et al. |
| 2012/0232398 A1 | 9/2012 | Roham et al. |
| 2012/0253140 A1 | 10/2012 | Addison et al. |
| 2012/0296219 A1 | 11/2012 | Chon et al. |
| 2012/0310051 A1 | 12/2012 | Addison et al. |
| 2013/0137936 A1 | 5/2013 | Baker, Jr. et al. |
| 2013/0138002 A1 | 5/2013 | Weng et al. |
| 2013/0172767 A1 | 7/2013 | Dripps et al. |

FOREIGN PATENT DOCUMENTS

| | | |
|---|---|---|
| EP | 1507474 B1 | 2/2009 |
| WO | WO 00/21438 | 4/2000 |
| WO | WO 03/000125 A1 | 1/2003 |
| WO | WO 03/055395 A1 | 7/2003 |
| WO | WO 03/084396 A1 | 10/2003 |
| WO | WO 04/075746 A2 | 9/2004 |
| WO | WO 2008/135985 A1 | 11/2008 |
| WO | WO 2009/043028 A2 | 4/2009 |
| WO | WO 2010/030238 A1 | 3/2010 |
| WO | WO 2010/135518 A1 | 11/2010 |
| WO | WO 2012/014065 A1 | 2/2012 |
| WO | WO 2012/051295 A2 | 4/2012 |

OTHER PUBLICATIONS

Lesurf, Jim. "FM & PM Demodulation." Oct. 2, 2007. https://web.archive.org/web/20071002193422/http://www.standrews.ac.uk/~www_pa/Scots_Guide/RadCom/part13/page1.html.

Stagg and Gennser, "Electronic analysis of foetal breathing movements: A practical application of phase-locked-loop principles," Journal of Med. Eng. and Tech., Sep. 1978, vol. 2, No. 5, pp. 246-249.

Rapaport and Cousin, "New phase-lock tracking instrument for foetal breathing monitoring," Med. & Biol. Eng. & Camp. 1982, vol. 20, pp. 1-6.

Lindberg, L.G., Ughall, H., Oberg, P.A., "Monitoring of respiratory and heart rates using a fibre-optic sensor," Medical & Biological Engineering & Computing, Sep. 1992, pp. 533-537.

International Search Report and Written Opinion of the International Searching Authority for Application No. PCT/US2013/020338, dated Apr. 11, 2013. 6 pages.

Addison, Paul S. et al., "Developing an Algorithm for Pulse Oximetry Derived Respiratory Rate (RRoxi): A Healthy Volunteer Study," Journal of Clinical Monitoring & Computing, 2012, 26: 45-51.

International Search Report and Written Opinion of the International Searching Authority for application No. PCT/US2014/014875, dated May 15, 2014.

International Search Report and Written Opinion of the International Searching Authority for application No. PCT/US2014/014899, dated May 15, 2014.

Nguyen et al., "Comparison of two Methods for Demodulation of Pulse Signals—Application in Case of Central Sleep Apnea." Journal of Science and Technology, 49(1), 2011, pp. ISSN:0866-708X.

Supplementary European Search Report from the European Patent Office in European Patent Application No. 14749411, dated Aug. 10, 2016.

* cited by examiner

SYSTEMS AND METHODS FOR DETERMINING RESPIRATION INFORMATION USING PHASE LOCKED LOOP

CROSS-REFERENCE TO RELATED APPLICATION

This application is a continuation of U.S. patent application Ser. No. 13/343,389, filed Jan. 4, 2012, which is hereby incorporated by reference herein in its entirety.

FIELD OF THE DISCLOSURE

The present disclosure relates to physiological signal processing, and more particularly relates to determining a physiological parameter such as respiration information from a physiological signal using a phase locked loop.

SUMMARY

A patient monitoring system may be configured to determine physiological information such as respiration information from a physiological signal such as a photoplethysmograph (PPG) signal. For example, a PPG signal may exhibit amplitude and frequency modulation based on the respiration of a patient. The PPG signal may be input to a phase locked loop to generate a frequency demodulated signal and an amplitude demodulated signal.

An autocorrelation sequence may be generated for each of the frequency demodulated signal and the amplitude demodulated signal. The autocorrelation sequences may be combined, e.g., based on confidence metrics associated with the autocorrelation sequences. Physiological information such as respiration information may be determined based on the combined autocorrelation sequence.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

The present disclosure is directed to determining physiological information such as respiration information from a photoplethysmograph (PPG) signal. The PPG signal may exhibit amplitude and frequency modulation based on the respiration of a patient. A phase locked loop may be used to generate a frequency demodulated signal and an amplitude demodulated signal from the PPG signal. The phase locked loop may include an oscillator, a phase detector, and a low pass filter. The oscillator signal may be generated to approximate the PPG signal and may be phase shifted by $\pi/2$ to have a phase offset with the PPG signal. The phase detector may determine a phase and frequency difference between the PPG signal and the oscillator signal. The resulting phase detector output may include a component at approximately twice the PPG signal frequency and a component representing the phase difference between the two signals. The phase detector output may be low pass filtered, resulting in the output of the phase difference signal.

The phase difference signal may be fed back to the oscillator in order to adjust the phase and frequency of the oscillator signal to match the PPG signal. As the PPG signal changes over time, e.g., due to modulations caused by respiration, the phase difference signal will reflect these changes to allow the oscillator to track the PPG signal. The phase difference signal may therefore be representative of the respiration component of the PPG signal and may be used as the frequency demodulated signal.

The oscillator signal may also be phase shifted by $\pi/2$ again to match the phase of the PPG signal. The phase shifted oscillator signal may be multiplied with the PPG signal, with the resulting product signal emphasizing amplitude modulations caused by respiration. The resulting product signal may be low pass filtered, resulting in the amplitude demodulated signal. An autocorrelation sequence may be generated for each of the frequency demodulated signal and the amplitude demodulated signal. The autocorrelation sequences may be combined, and the combined autocorrelation sequence may be used to determine respiration information.

For purposes of clarity, the present disclosure is written in the context of the physiological signal being a PPG signal generated by a pulse oximetry system. It will be understood that any other suitable physiological signal or any other suitable system may be used in accordance with the teachings of the present disclosure.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations that are not typically understood to be optimal for pulse oximetry serve as suitable sensor locations for the monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t) = I_O(\lambda)\exp(-(s\beta_O(\lambda)+(1-s)\beta_r(\lambda))l(t)) \quad (1)$$

where:
$\lambda$=wavelength;
t=time;
I=intensity of light detected;
$I_0$=intensity of light transmitted;
s=oxygen saturation;
$\beta_O$, $\beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.
1. The natural logarithm of Eq. 1 is taken ("log" will be used to represent the natural logarithm) for IR and Red to yield $$\log I = \log I_o - (s\beta_o + (1-s)\beta_r)l. \quad (2)$$

2. Eq. 2 is then differentiated with respect to time to yield $$\frac{d\log I}{dt} = -(s\beta_O + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{d\log I(\lambda_R)/dt}{d\log I(\lambda_{IR})/dt} = \frac{s\beta_O(\lambda_R) + (1-s)\beta_r(\lambda_R)}{s\beta_O(\lambda_{IR}) + (1-s)\beta_r(\lambda_{IR})}. \quad (4)$$

4. Solving for s yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_O(\lambda_{IR}) - \beta_r(\lambda_{IR})) - \frac{d\log I(\lambda_{IR})}{dt}(\beta_O(\lambda_R) - \beta_r(\lambda_R))}. \quad (5)$$

5. Note that, in discrete time, the following approximation can be made:

$$\frac{d\log I(\lambda, t)}{dt} \simeq \log I(\lambda, t_2) - \log I(\lambda, t_1). \quad (6)$$

6. Rewriting Eq. 6 by observing that log A−log B=log(A/B) yields $$\frac{d\log I(\lambda, t)}{dt} \simeq \log\left(\frac{I(t_2, \lambda)}{I(t_1, \lambda)}\right). \quad (7)$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (8)$$

where R represents the "ratio of ratios."
8. Solving Eq. 4 for s using the relationship of Eq. 5 yields $$s = \frac{\beta_r(\lambda_R) - R\beta_r(\lambda_{IR})}{R(\beta_O(\lambda_{IR}) - \beta_r(\lambda_{IR})) - \beta_O(\lambda_R) + \beta_r(\lambda_R)}. \quad (9)$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{dI/dt}{I}, \quad (10)$$

Eq. 8 becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}}, \quad (11)$$

$$= \frac{[I(t_2, \lambda_R) - I(t_1 - \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R when $$x=[I(t_2,\lambda_{IR})-I(t_1,\lambda_{IR})]I(t_1,\lambda_R), \quad (12)$$

and $$y=[I(t_2,\lambda_R)-I(t_1,\lambda_R)]I(t_1,\lambda_{IR}). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

Figure 1:
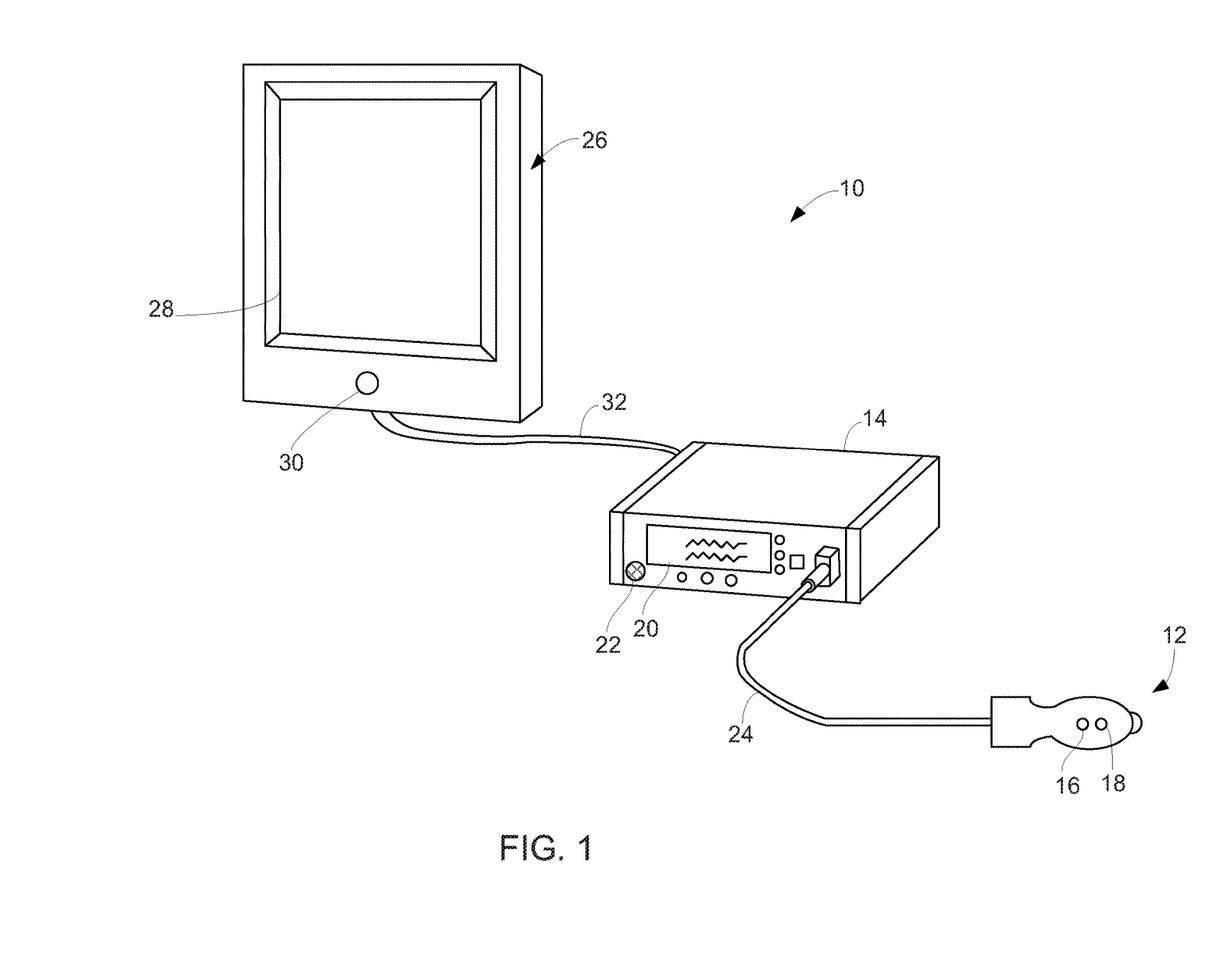
FIG. 1 shows an illustrative patient monitoring system in accordance with some embodiments of the present disclosure.

FIG. 1 is a perspective view of an embodiment of a patient monitoring system 10. System 10 may include sensor unit 12 and monitor 14. In some embodiments, sensor unit 12 may be part of an oximeter. Sensor unit 12 may include an emitter 16 for emitting light at one or more wavelengths into a patient's tissue. A detector 18 may also be provided in sensor unit 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a patient's forehead, while a second sensor unit may be positioned at a patient's fingertip.

Sensor units may each detect any signal that carries information about a patient's physiological state, such as an electrocardiograph signal, arterial line measurements, or the pulsatile force exerted on the walls of an artery using, for example, oscillometric methods with a piezoelectric transducer. According to another embodiment, system 10 may include two or more sensors forming a sensor array in lieu of either or both of the sensor units. Each of the sensors of a sensor array may be a complementary metal oxide semiconductor (CMOS) sensor. Alternatively, each sensor of an array may be charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In some embodiments, emitter 16 and detector 18 may be arranged so that light from emitter 16 penetrates the tissue and is reflected by the tissue into detector 18, such as in a sensor designed to obtain pulse oximetry data from a patient's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood oxygen saturation, and respiration information) based at least in part on data relating to light emission and detection received from one or more sensor units such as sensor unit 12 and an additional sensor (not shown). In some embodiments, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may be allow communication between monitor 14 and sensor unit 12.

Patient monitoring system 10 may also include display monitor 26. Monitor 14 may be in communication with display monitor 26. Display monitor 26 may be any electronic device that is capable of communicating with monitor 14 and calculating and/or displaying physiological parameters, e.g., a general purpose computer, tablet computer, smart phone, or an application-specific device. Display monitor 26 may include a display 28 and user interface 30. Display 28 may include touch screen functionality to allow a user to interface with display monitor 26 by touching display 28 and utilizing motions. User interface 30 may be any interface that allows a user to interact with display monitor 26, e.g., a keyboard, one or more buttons, a camera, a microphone, or a touchpad.

Monitor 14 and display monitor 26 may communicate utilizing any suitable transmission medium, including wireless (e.g., WiFi, Bluetooth, etc.), wired (e.g., USB, Ethernet, etc.), or application-specific connections. In an exemplary embodiment, monitor 14 and display monitor 26 may be connected via cable 32. Monitor 14 and display monitor 26 may communicate utilizing standard or proprietary communications protocols, such as the Standard Host Interface Protocol (SHIP) developed and used by Covidien of Mansfield, Mass. In addition, monitor 14, display monitor 26, or both may be coupled to a network to enable the sharing of information with servers or other workstations (not shown). Monitor 14, display monitor 26, or both may be powered by a battery (not shown) or by a conventional power source such as a wall outlet.

Monitor 14 may transmit calculated physiological parameters (e.g., pulse rate, blood oxygen saturation, and respiration information) to display monitor 26. In some embodiments, monitor 14 may transmit a PPG signal, data representing a PPG signal, or both to display monitor 26, such that some or all calculated physiological parameters (e.g., pulse rate, blood oxygen saturation, and respiration information) may be calculated at display monitor 26. In an exemplary embodiment, monitor 14 may calculate pulse rate and blood oxygen saturation, while display monitor 26 may calculate respiration information such as a respiration rate.

Figure 2:
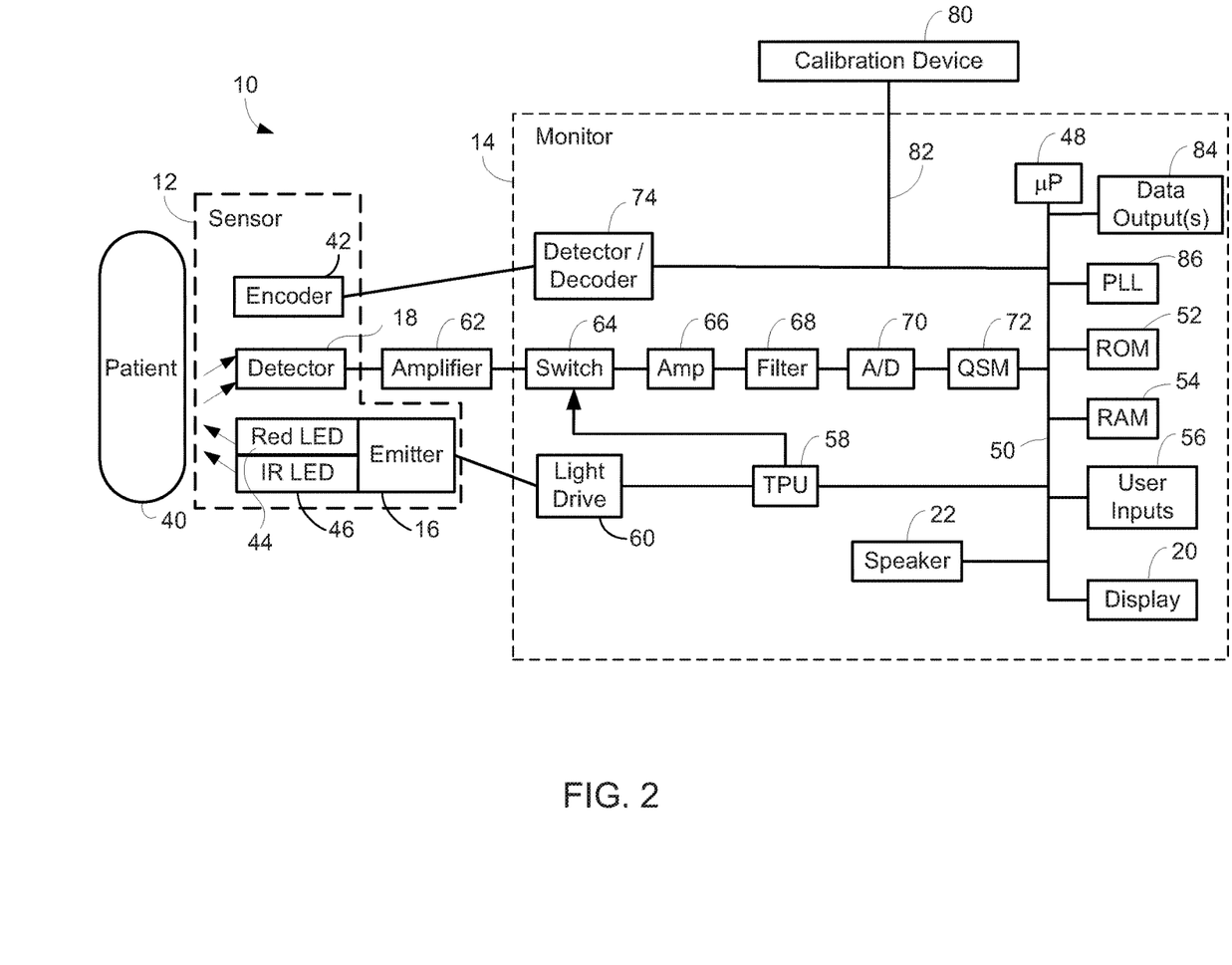
FIG. 2 is a block diagram of the illustrative patient monitoring system of FIG. 1 coupled to a patient in accordance with some embodiments of the present disclosure.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor may emit only a Red light while a second sensor may emit only an IR light. In a further example, the wavelengths of light used may be selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In some embodiments, encoder 42 may contain information about sensor unit 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which measurements may be determined based at least in part on the signal or signals received at sensor unit 12. For example, some pulse oximetry sensors rely on equations to relate an area under a portion of a PPG signal corresponding to a physiological pulse to determine blood pressure. These equations may contain coefficients that depend upon a patient's physiological characteristics as stored in encoder 42. Encoder 42 may, for instance, be a coded resistor that stores values corresponding to the type of sensor unit 12 or the type of each sensor in the sensor array, the wavelengths of light emitted by emitter 16 on each sensor of the sensor array, and/or the patient's characteristics. In some embodiments, encoder 42 may include a memory on which one or more of the following information may be stored for communication to monitor 14; the type of the sensor unit 12; the wavelengths of light emitted by emitter 16; the particular wavelength each sensor in the sensor array is monitoring; a signal threshold for each sensor in the sensor array; any other suitable information; or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, data output 84, phase locked loop (PLL) 86, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In some embodiments, microprocessor 48 may determine the patient's physiological parameters, such as $SpO_2$, pulse rate, and/or respiration information, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable the microprocessor to determine the thresholds based at least in part on algorithms or look-up tables stored in ROM 52. In some embodiments, user inputs 56 may be used to enter information, select one or more options, provide a response, input settings, any other suitable inputting function, or any combination thereof. User inputs 56 may be used to enter information about the patient, such as age, weight, height, diagnosis, medications, treatments, and so forth. In some embodiments, display 20 may exhibit a list of values, which may generally apply to the patient, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Phase locked loop ("PLL") 86 may track the phase and frequency of a PPG signal or a signal derived from the PPG signal, PLL 86 may generate a frequency demodulated signal and an amplitude demodulated signal, or may generate signals used to generate a frequency demodulated signal and amplitude demodulated signal. PLL 86 will be described as receiving a PPG signal as an input. It will be understood that PPG signal as described herein includes any signal derived from a PPG signal that includes PPG information, e.g., a signal derived from the PPG signal such as a filtered PPG signal or a derivative or second derivative of the PPG signal. It will also be understood that PLL 86 may track and demodulate any physiological signal in addition to a PPG signal. Although PLL 86 may track the PPG signal and generate demodulated signals in any suitable manner, in an exemplary embodiment PLL may be implemented as described in FIG. 4. PLL 86 may be a component of monitor 14 or display monitor 26. PLL 86 may be implemented with hardware, software (e.g., running on microprocessor 48), or a combination of hardware and software. Accordingly, in some embodiments PLL 86 may be integral to microprocessor 48. PLL 86 may be implemented in any suitable manner on display monitor 26, e.g., as hardware, software (e.g., running on a microprocessor or general purpose computer of display monitor 26), or a combination of hardware and software.

Data output 84 may provide for communications with other devices such as display monitor 26 utilizing any suitable transmission medium, including wireless (e.g., WiFi, Bluetooth, etc.), wired (e.g., USB, Ethernet, etc.), or application-specific connections. Data output 84 may receive messages to be transmitted from microprocessor 48 via bus 50. Exemplary messages to be sent in an embodiment described herein may include PPG signals to be transmitted to display monitor module 26.

The optical signal attenuated by the tissue of patient 40 can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. Also, because blood is a fluid, it responds differently than the surrounding tissue to inertial effects, which may result in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals, control the amount of noise present in the signal, or otherwise identify noise components in order to prevent them from affecting measurements of physiological parameters derived from the sensor signals.

Figure 3:
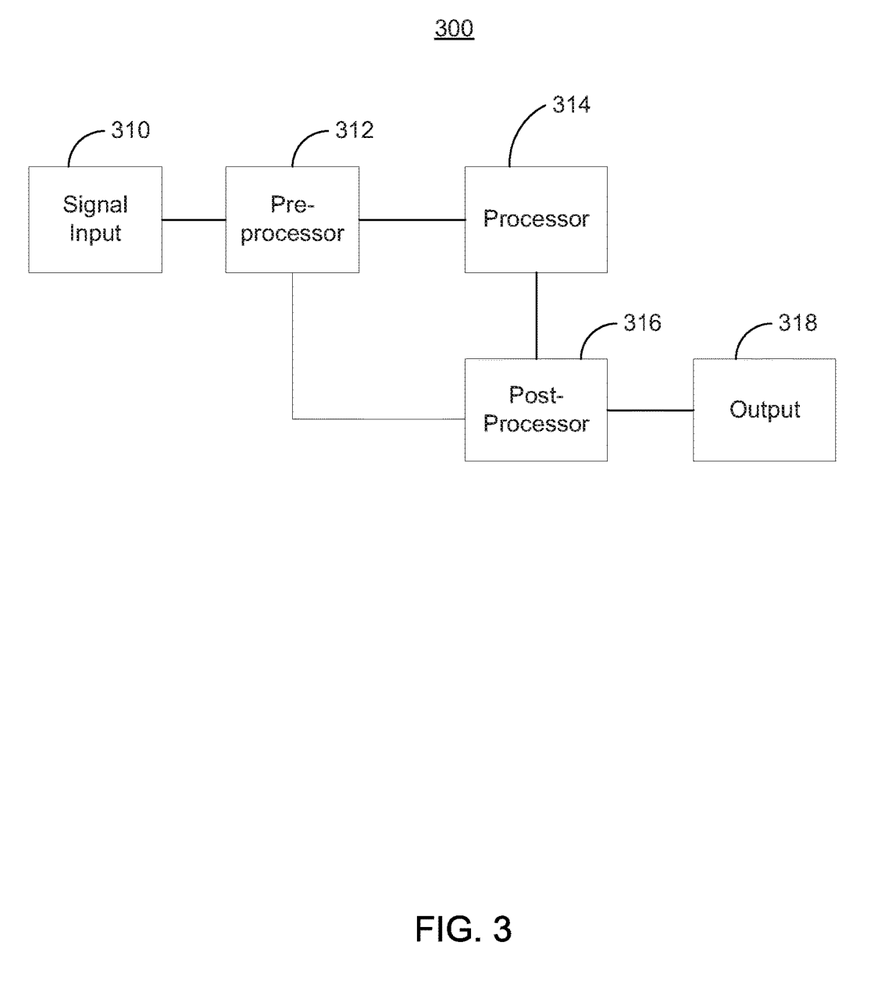
FIG. 3 shows a block diagram of an illustrative signal processing system in accordance with some embodiments of the present disclosure.

FIG. 3 is an illustrative processing system 300 in accordance with an embodiment that may implement the signal processing techniques described herein. In some embodiments, processing system 300 may be included in a patient monitoring system (e.g., patient monitoring system 10 of FIGS. 1-2). Processing system 300 may include input signal 310, pre-processor 312, processor 314, post-processor 316, and output 318. Pre-processor 312, processor 314, and post-processor 316 may be any suitable software, firmware, hardware, or combination thereof for calculating physiological parameters such as respiration information based on input signal 310. For example, pre-processor 312, processor 314, and post-processor 316 may include one or more hardware processors (e.g., integrated circuits), one or more software modules, computer-readable media such as memory, firmware, or any combination thereof. Pre-processor 312, processor 314, and post-processor 316 may, for example, be a computer or may be one or more chips (i.e., integrated circuits). Pre-processor 312, processor 314, and post-processor 316 may, for example, include an assembly of analog electronic components.

In some embodiments, processing system 300 may be included in monitor 14 and/or display monitor 26 of a patient monitoring system (e.g., patient monitoring system 10 of FIGS. 1-2). In the illustrated embodiment, input signal 310 may be a PPG signal. Input signal 310 may be a PPG signal that was sampled and generated at monitor 14, for example at 76 Hz. Input signal 310, pre-processor 312, processor 314, and post-processor 316 may reside entirely within a single device (e.g., monitor 14 or display monitor 26) or may reside in multiple devices (e.g., monitor 14 and display monitor 26).

Input signal 310 may be coupled to pre-processor 312. In some embodiments, input signal 310 may include PPG signals corresponding to one or more light frequencies, such as a Red PPG signal and an IR PPG signal. In some embodiments, the signal may include signals measured at one or more sites on a patient's body, for example, a patient's finger, toe, ear, arm, or any other body site. In some embodiments, signal 310 may include multiple types of signals (e.g., one or more of an ECG signal, an EEG signal, an acoustic signal, an optical signal, a signal representing a blood pressure, and a signal representing a heart rate). The signal may be any suitable biosignal or signals, such as, for example, electrocardiogram, electroencephalogram, electrogastrogram, electromyogram, heart rate signals, pathological sounds, ultrasound, or any other suitable biosignal. The systems and techniques described herein are also applicable to any dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, and/or any combination thereof.

Pre-processor 312 may be implemented by any suitable combination of hardware and software. In an embodiment, pre-processor 312 may be any suitable signal processing device and the signal received from input signal 310 may include one or more PPG signals. An exemplary received PPG signal may be received in a streaming fashion, or may be received on a periodic basis as a sampling window, e.g., every 5 seconds. In an exemplary embodiment, analysis of input signal 310 may be based on an analysis window of a series of recently received PPG signal sampling windows, e.g., a 45-second analysis window may correspond to the 9 most recent 5-second sampling windows. The received signal may include the PPG signal as well as other information related to the PPG signal, e.g., a pulse found indicator, the mean pulse rate from the PPG signal, the most recent pulse rate, an indicator for the most recent invalid sample, and an indicator of the last artifact for the PPG signal. It will be understood that input signal 310 may include any suitable signal source, signal generating data, signal generating equipment, or any combination thereof to be provided to pre-processor 312. The signal received at input signal 310 may be a single signal, or may be multiple signals transmitted over a single pathway or multiple pathways.

Pre-processor 312 may apply one or more signal processing operations to input signal 310. For example, pre-processor 312 may apply a pre-determined set of processing operations to input signal 310 to produce a signal that may be appropriately analyzed and interpreted by processor 314, post-processor 316, or both. Pre-processor 312 may perform any necessary operations to provide a signal that may be used as an input for processor 314 and post-processor 316 to determine physiological information such as respiration information. Examples include reshaping the signal for transmission, multiplexing the signal, modulating the signal onto carrier signals, compressing the signal, encoding the signal, filtering the signal, low-pass filtering, band-pass filtering, signal interpolation, downsampling of a signal, attenuating the signal, adaptive filtering, closed-loop filtering, any other suitable filtering, and/or any combination thereof.

Other signal processing operations may be performed by pre-processor 312 and may be related to extracting respiration information from the PPG signal. In an exemplary embodiment, pre-processor 312 may include a PLL for generating a frequency demodulated signal, an amplitude demodulated signal, or both, from the PPG signal as described herein. In another embodiment, pre-processor 312 may also produce one or more morphology metric values. Morphology metrics may be parameters that may be calculated from the PPG signal that provide information related to respiration. Examples include a down metric for a pulse, kurtosis for a pulse, the delta of the second derivative between predetermined samples of consecutive pulses, the up metric for a pulse, skew, ratio of predetermined samples of a pulse or its first or second derivative (e.g., b/a ratio or c/a ratio), peak amplitude of a pulse, center of gravity of a pulse, or area of a pulse, as described in more detail herein.

The demodulated signals, morphology metric signals (generated from the morphology metric values as described herein), or any combination thereof, may be used to determine respiration information as described herein. It will be understood that while generating the demodulated signals and morphology metric values may be described with respect to pre-processor 312, these operations may also be performed by processor 314, or a combination of pre-processor 312 and processor 314. Other information that may be determined by pre-processor 312 may include the pulse rate, the variability of the period of the PPG signal, the variability of the amplitude of the PPG signal, and an age measurement indicative of the age of the useful portion of the analyzed PPG signal.

In some embodiments, pre-processor 312 may be coupled to processor 314 and post-processor 316. Processor 314 and post-processor 316 may be implemented by any suitable combination of hardware and software. Processor 314 may receive physiological information and calculated parameters from pre-processor 312. For example, processor 314 may receive a frequency demodulated signal, an amplitude demodulated signal, or both. In another embodiment, processor 314 may receive a PPG signal, and may generate a frequency demodulated signal, an amplitude demodulated signal, or both, using a PLL. In another embodiment processor 314 may also receive one or more sets morphology metric values. The morphology metric values may be used to generate one or more morphology metric signals.

Processor 314 may utilize the received demodulated signals to determine respiration information. In an exemplary embodiment, an autocorrelation sequence may be generated for each of the frequency demodulated signal and the amplitude demodulated signal. A confidence metric may be generated for each of the autocorrelation sequences, e.g., based on a measure of the periodicity of the autocorrelation sequence. A combined autocorrelation sequence may be generated from the autocorrelation sequences, e.g., based on a confidence metric associated with each of the autocorrelation sequences. In another embodiment, one or more autocorrelation sequences may also be generated for one or more of the morphology metric signals. The morphology based autocorrelation sequence may be combined with the demodulated signal based autocorrelation sequence, e.g., based on a confidence metric associated with the one or more morphology metric signals. Respiration information may be determined from the combined autocorrelation sequence.

Processor 314 may be coupled to post-processor 316 and may communicate respiration information to post-processor 316. Processor 314 may also provide other information to post-processor 316 such as the signal age related to the signal used to calculate the respiration information, a time ratio representative of the useful portion of the respiration information signal, or a confidence metric indicative of the strength of the respiration information signals. Pre-processor 312 may also provide information to post-processor 316 such as period variability, amplitude variability, and pulse rate information. Post-processor 316 may utilize the received information to calculate an output respiration information, as well as other information such as the age of the respiration information and status information relating to the respiration information output, e.g., whether a valid output respiration information value is currently available. In an embodiment, a current respiration information value may be combined with one or more previously determined respiration information values, e.g., based on a confidence metric or similar weighting factor. Post-processor 316 may provide the output information to output 318.

Output 318 may be any suitable output device such as one or more medical devices (e.g., a medical monitor that displays various physiological parameters, a medical alarm, or any other suitable medical device that either displays physiological parameters or uses the output of post-processor 316 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

In some embodiments, all or some of pre-processor 312, processor 314, and/or post-processor 316 may be referred to collectively as processing equipment. For example, processing equipment may be configured to amplify, filter, sample and digitize an input signal 310 and calculate physiological information from the signal.

Pre-processor 312, processor 314, and post-processor 316 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by pre-processor 312, processor 314, and post-processor 316 to, for example, store data relating to input PPG signals, morphology metrics, respiration information, or other information corresponding to physiological monitoring.

It will be understood that system 300 may be incorporated into system 10 (FIGS. 1 and 2) in which, for example, input signal 310 may be generated by sensor unit 12 (FIGS. 1 and 2) and monitor 14 (FIGS. 1 and 2). Pre-processor 312, processor 314, and post-processor 316 may each be located in one of monitor 14 or display monitor 26 (or other devices), and may be split among multiple devices such as monitor 14 or display monitor 26. In some embodiments, portions of system 300 may be configured to be portable. For example, all or part of system 300 may be embedded in a small, compact object carried with or attached to the patient (e.g., a watch, other piece of jewelry, or a smart phone). In some embodiments, a wireless transceiver (not shown) may also be included in system 300 to enable wireless communication with other components of system 10 (FIGS. 1 and 2). As such, system 10 (FIGS. 1 and 2) may be part of a fully portable and continuous patient monitoring solution. In some embodiments, a wireless transceiver (not shown) may also be included in system 300 to enable wireless communication with other components of system 10. For example, communications between one or more of pre-processor 312, processor 314, and post-processor 316 may be over BLUETOOTH, 802.11, WiFi, WiMax, cable, satellite, Infrared, or any other suitable transmission scheme. In some embodiments, a wireless transmission scheme may be used between any communicating components of system 300.

Figure 4:
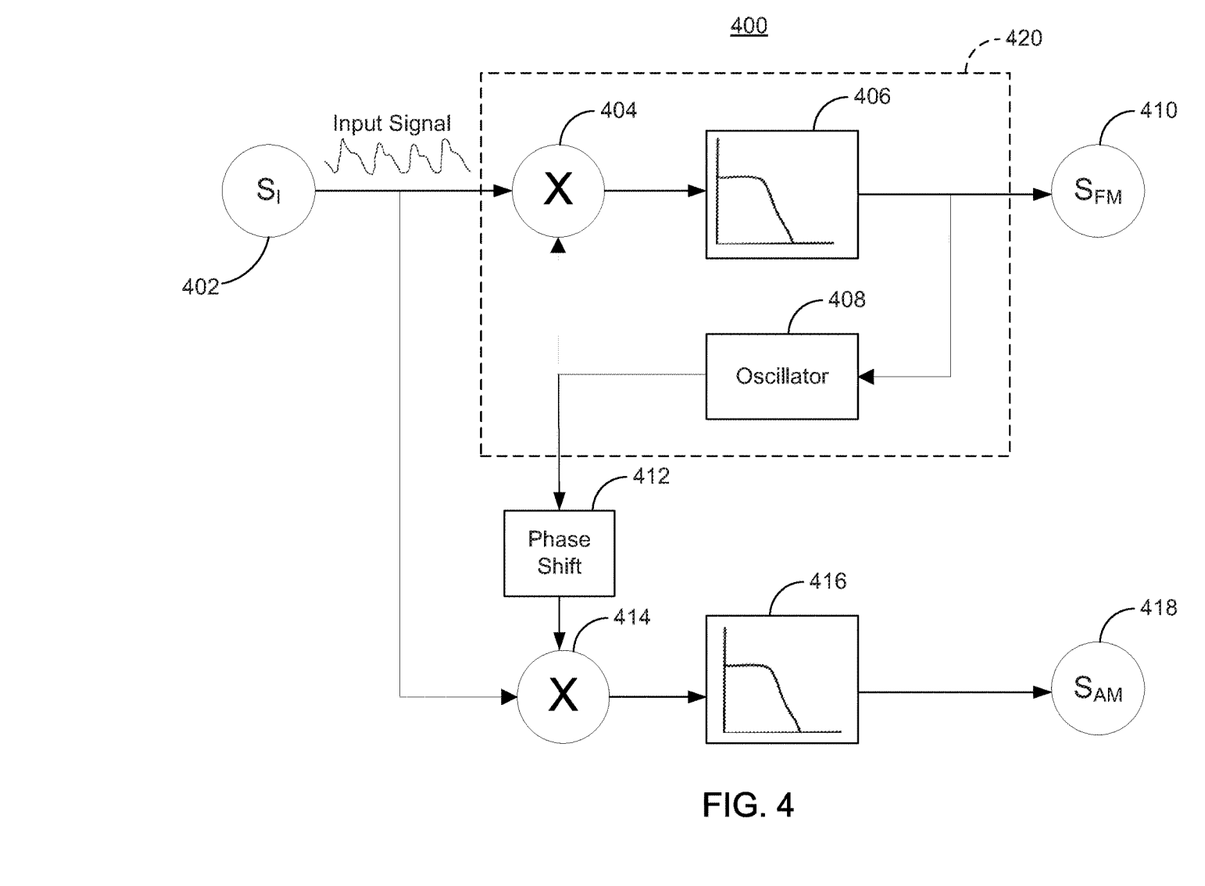
FIG. 4 is a flow diagram showing steps for using a phase locked loop to generate a frequency demodulated signal and an amplitude demodulated signal from a physiological signal in accordance with some embodiments of the present disclosure.

FIG. 4 is a flow diagram showing steps for using a phase locked loop 420 to generate a frequency demodulated signal and an amplitude demodulated signal from a physiological signal in accordance with some embodiments of the present disclosure. Although it will be understood that the frequency demodulated signal and amplitude demodulated signal may be generated in any suitable manner, in an exemplary embodiment they may be generating using the PLL arrangement of FIG. 4. The PLL arrangement of FIG. 4 may be implemented as part of pre-processor 312, processor 314, or both, and may be located within monitor 14, display monitor 26, or both.

PLL 420 may receive an input PPG signal 402 at phase detector 404. It will be understood that PPG signal 402 as described herein includes any signal derived from a PPG signal that includes PPG data, e.g., a signal derived from the PPG signal such as a filtered PPG signal or a derivative of the PPG signal. PPG signal may represent an analysis window of received PPG data, e.g., 45 seconds of PPG data. Phase detector 404 may compare the phase of input signal 402 with the phase of an oscillator signal generated by oscillator 408. Phase detector may be any suitable hardware, software, or combination of hardware and software that generates a phase detector output signal based on the phase difference between the two input signals. Exemplary embodiments of a phase detector include a multiplier, an exclusive-OR operator, a flip-flop, a digital multiplier and a sampler driven by the input PPG signal 402 to sample the oscillator signal, or a sampler driven by the oscillator signal to sample the input PPG signal 402.

In an exemplary embodiment, phase detector 404 may be a multiplier and the oscillator signal may be an approximation of PPG signal 402 phase shifted by $\pi/2$. The resulting phase detector output signal may include multiple components having different frequencies, including a component at approximately twice the frequency of the input signal and a component representing the phase difference between PPG signal 402 and the oscillator signal. The phase detector output signal may be input to low pass filter 406. Low pass filter 406 may include hardware, software, or a combination of hardware and software. Although low pass filter 406 may be implemented in any suitable manner, in an exemplary embodiment the low pass filter 406 may be configured to filter any frequency components having a frequency exceeding an expected phase difference between PPG signal 402 and the oscillator signal. Low pass filter 402 may have a fixed cut off frequency or the cut off frequency may be dynamic based on PPG signal 402, e.g., based on a percentage of the frequency of PPG signal 402. In the exemplary embodiment described herein, low pass filter 406 may be configured to reject components of the phase detector output signal that are not related to the phase difference between PPG signal 402 and the oscillator signal, e.g., the component of the phase detector output signal having a frequency at approximately twice the PPG signal frequency.

The value of the resulting phase difference signal may change based on whether the oscillator signal leads or lags PPG signal 402, and based on the degree of the lead or lag. As will be described herein, oscillator 408 may attempt to match the phase and frequency of PPG signal 402. To the extent that the phase and frequency of PPG signal 402 change over time, the resulting phase difference signal will reflect those changes such that oscillator 408 may continue to track PPG signal 402. This phase difference signal may correspond to frequency changes in the PPG signal that are the result of respiration, which may typically occur at a frequency of approximately 10-40% of the frequency associated with the pulse rate indicated by PPG signal 402. Accordingly, the phase difference signal may be output as a frequency demodulated signal 410. Frequency demodulated signal may comprise the phase difference signal or may be derived from the phase difference signal, e.g., based on additional filtering operations such as a band pass filter about a range of interest related to respiration (not depicted). Frequency demodulated signal 410 may be stored to be used for determining respiration information. In an exemplary embodiment, a complete analysis window (e.g., 45 seconds of data) of frequency demodulated signal 410 may be stored.

The phase difference signal may also be input to oscillator 408. Oscillator 408 may be implemented in any suitable manner, including as software, hardware, or a combination of software and hardware. In an exemplary embodiment oscillator 408 may be a voltage controlled oscillator, wherein the oscillator 408 phase and frequency are modified based on the input voltage of the phase difference signal. In another embodiment, oscillator 408 may be a modulo-N counter having a length (N) controlled by the phase difference signal. The oscillator signal output of oscillator 408 may be configured to approximate a waveform shape of PPG signal 402, e.g., by varying the duty cycle of the oscillator signal. In an exemplary embodiment the oscillator signal may also be generated to have a $\pi/2$ phase difference with PPG signal 402. The oscillator signal may be fed back to phase detector 404 to be compared to the latest samples of PPG signal 402.

The oscillator signal may also be coupled to phase shifter 412, which may shift the phase of the oscillator signal in a manner suitable to generate an amplitude demodulated signal based on PPG signal 402. Phase shifter may be implemented in any suitable manner, including as software, hardware, or a combination of software and hardware. Although the oscillator signal may be phase shifted in any suitable manner, in an exemplary embodiment the oscillator signal may be shifted by $\pi/2$ such that it is substantially in phase with PPG signal 402. The phase shifted oscillator signal and PPG signal 402 may then be utilized to generate an amplitude demodulated signal. In an exemplary embodiment the phase shifted oscillator signal may be multiplied with PPG signal 402 by multiplier 414. Because the signals may be substantially in phase, amplitude modulations may be emphasized based on the multiplication. The output product signal from multiplier 414 may be low pass filtered by low pass filter 416. Low pass filter 416 may have a fixed cut off frequency or the cut off frequency may be dynamic based on PPG signal 402, e.g., based on a percentage of the frequency of PPG signal 402. The output from low pass filter 416 constitutes the amplitude demodulated signal 418. Amplitude demodulated signal 418 may be stored to be used for determining respiration information. In an exemplary embodiment, a complete analysis window (e.g., 45 seconds of data) of amplitude demodulated signal 418 may be stored.

Figure 5:
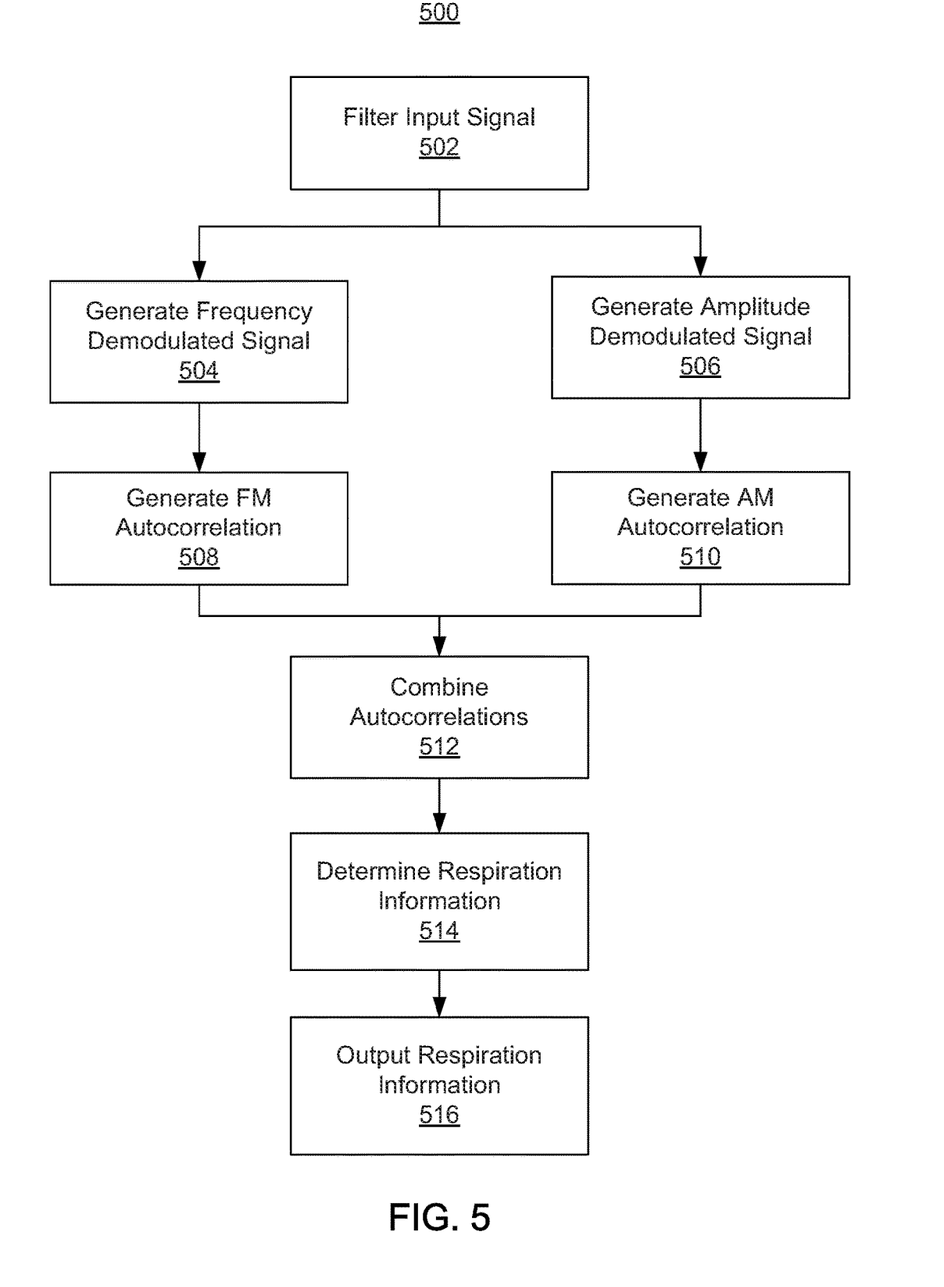
FIG. 5 is a flow diagram showing illustrative steps for determining respiration information from a photoplethysmograph signal in accordance with some embodiments of the present disclosure.

FIG. 5 is a flow diagram showing illustrative steps for determining a physiological parameter such as respiration information from a physiological signal such as a PPG signal in accordance with some embodiments of the present disclosure. Although an exemplary embodiment is described herein, it will be understood that each of steps 500 may be performed by pre-processor 312, processor 314, post-processor 316, or any combination thereof. It will also be understood that steps 500 may be performed in alternative sequence or in parallel, that steps may be omitted, and that additional steps may be added or inserted.

At step 502 pre-processor 312 or processor 314 may filter an input signal such as a PPG signal. Although the PPG may be filtered in any suitable manner, in an exemplary embodiment the PPG signal may be band pass filtered based around the heart rate. In an exemplary embodiment, the filter range may be fixed based on a normal range of heart range values, or may be variable based on the pulse rate associated with the analysis window of PPG data being analyzed.

At step 504 pre-processor 312, processor 314, or both, may generate a frequency demodulated signal using the PLL of FIG. 4 as described herein for an analysis window of PPG data. At step 506 pre-processor 312, processor 314, or both, may generate an amplitude demodulated signal using the PLL of FIG. 4 as described herein for an analysis window of PPG data. Although in the exemplary embodiment depicted in FIG. 5 both a frequency demodulated signal and amplitude demodulated signal are generated, respiration information may also be determined based on only one of the demodulated signals.

In addition to generating the frequency demodulated signal and/or the amplitude demodulated signal, in an embodiment one or more morphology metric signals may be generated (not depicted). Pre-processor 312 may identify fiducial points for successive pulse waves of a PPG signal. Fiducial points may be identified in any suitable manner, for example based on peaks, troughs, slope values (e.g., the maximum slope of the PPG signal), and/or predetermined offsets. An example of determining fiducial points for a PPG signal is described in more detail in co-pending, commonly assigned U.S. patent application Ser. No. 13/243,907, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety. The fiducial points may define a series of fiducial defined portions that may be used as a reference for subsequent calculations, e.g., of morphology metric signals. Pre-processor 312 may generate morphology metrics from the PPG signal. Morphology metrics may be calculated from the PPG signal in any suitable manner. In one embodiment, a plurality of morphology metrics may be generated from the PPG signal. Example morphology metrics that may be relevant to determining a physiological parameter such as respiration information from a PPG signal may include a down metric, a kurtosis metric, a delta of second derivative (DSD) metric, an up metric, a skew metric, a ratio of samples metric (e.g., a b/a ratio metric or c/a ratio metric), a i_b metric, a peak amplitude metric, a center of gravity metric, and an area metric. For each morphology metric a sequence of morphology metric values, each corresponding to a fiducial defined region, may be calculated. The sequences of morphology metric values may be communicated to processor 314 to be attenuated, interpolated, and filtered to generate the morphology metric signals. Generating morphology metric signals from a PPG signal is described in more detail in co-pending, commonly assigned U.S. patent application Ser. No. 13/243,853, filed Sep. 23, 2011 and entitled "SYSTEMS AND METHODS FOR DETERMINING RESPIRATION INFORMATION FROM A PHOTOPLETHYSMO-GRAPH," which is incorporated by reference herein in its entirety.

Pre-processor 312 may determine a usable portion of the PPG signal (not depicted). Portions of the received signal may include samples with values that are unlikely to reflect actual values as a result of inaccurate measurement, user error, or other factors. Input signal 310 may be analyzed to identify divergences in the signal baseline, motion artifacts, divergences in pulse period, and any other signal features that may indicate inaccurate measurement, user error, or other factors. Based on this analysis, pre-processor 312 may identify portions of the input signal 310 to be ignored by processor 314 in calculating values such as respiration information. In an embodiment, only those portions of the frequency demodulated signal, amplitude demodulated signal, or the morphology metric signals that correspond to the usable portion of the input signal may be used to generate an autocorrelation sequence by processor 314.

At steps 508 and 510, processor 314 may generate an autocorrelation sequence for each of the demodulated signals. Autocorrelation is the cross-correlation of a signal with itself, and to the extent that the underlying signal includes regular or repeating patterns the peaks of the resulting autocorrelation sequence may correspond to periodic components of the underlying signal. The autocorrelations of the demodulated signals (and the one or more morphology metric signals if those are also generated) may be utilized to determine respiration information such as respiration rate as described herein. The formula for the autocorrelation is the following:

$$R_{xx}(m) = \Sigma_{n \in S} x(n) \times (n-m), \text{ for } m = -M, \ldots, M \quad (14)$$

where:
S=the signal support of the finite segment;
n=the sample of the signal;
m=the lag; and
M=the maximum lag computed for the autocorrelation.

For real signals with a maximum point located at the central point of the autocorrelation (i.e., where the signal is being compared directly with itself without any time lag) the autocorrelation sequence may be symmetric about the central point. Accordingly, it may be possible to calculate the autocorrelation for one half of the overall lag about zero (e.g., from −M to 0, or from 0 to M) and duplicate the result about the central point. Accordingly, the autocorrelation sequence may be calculated as follows:

$$R_{xx}(m) = \begin{cases} \sum_{n=0}^{min(max(L-m,0),L)} x(n+m)x(n), \text{ for } m = 0, \ldots, M \\ R_{xx}(-m), \text{ for } m = -M, \ldots, -1 \end{cases} \quad (15)$$

A confidence metric may also be calculated at steps 508 and 510 for each of the autocorrelation sequences. A confidence metric may be based on the regularity or periodicity of the underlying demodulated signals (and morphology metric signals, if used) based on the autocorrelation sequence. For example, the autocorrelation sequence will have larger magnitude (positive or negative) repeating peaks if a signal is regular or periodic. Although a confidence metric may be determined in any suitable manner, in an exemplary embodiment the magnitude of any local maxima or minima of the autocorrelation sequence may be used to generate a confidence metric.

At step 512, processor 314 may combine the autocorrelation sequences to generate a combined autocorrelation sequence, if more than one autocorrelation sequence is generated. Although the autocorrelation sequences may be combined in any suitable manner, in an exemplary embodiment the contribution of each autocorrelation sequence to the combined autocorrelation sequence may be based on the confidence metric associated with each autocorrelation sequence. An exemplary embodiment for the generating a combined autocorrelation sequence is described in more detail in co-pending, commonly assigned U.S. patent application Ser. No. 13/243,951, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety.

At step 514, processor 314 may determine respiration information based on the combined autocorrelation sequence, or a single autocorrelation sequence if only one autocorrelation sequence is generated. Respiration information may be determined from the autocorrelation sequence in any suitable manner. In one exemplary embodiment, a continuous wavelet transform may be used to determine respiration information such as respiration rate from the autocorrelation sequence, as is described in more detail in co-pending, commonly assigned U.S. patent application Ser. No. 13/243,892, filed Sep. 23, 2011 and entitled "SYSTEMS AND METHODS FOR DETERMINING RESPIRATION INFORMATION FROM A PHOTOPLETHYSMO-GRAPH," which is incorporated by reference herein in its entirety. In another exemplary embodiment, respiration information may be determined directly from the autocorrelation sequence, e.g., by comparing the peaks of the autocorrelation sequence to a threshold value or by identifying a maximum peak of the autocorrelation sequence within a window of interest. Determining respiration information directly from the autocorrelation sequence is described in more detail in co-pending, commonly assigned U.S. patent application Ser. No. 13/243,785, filed Sep. 23, 2011 and entitled "SYSTEMS AND METHODS FOR DETERMINING RESPIRATION INFORMATION FROM A PHOTOPLETHYSMOGRAPH," which is incorporated by reference herein in its entirety. As is described in more detail herein, the determination of respiration information may be modified based on a historical distribution of respiration values. The output respiration value may be communicated to post-processor 316.

At step 516, post-processor 316 may determine an output respiration value to be displayed, e.g., at the patient monitoring system. The display respiration value may be determined in any suitable manner. For example, the display respiration value may be based on the currently received respiration value. In another exemplary embodiment, the display respiration value may be based on the received respiration value as well as previously received respiration values. In an exemplary embodiment, post-processor 316 may calculate the display respiration value from the respiration value for the current analysis window and respiration values for one or more previous analysis windows, e.g., the five previous analysis windows.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A method for determining respiration rate using a patient monitor, the method comprising:
   receiving a photoplethysmograph (PPG) signal;
   generating, using the patient monitor, an oscillator signal;
   generating, using the patient monitor, a phase-shifted oscillator signal based on a phase difference between the PPG signal and the oscillator signal;
   generating, using the patient monitor, an amplitude demodulated signal by multiplying the phase-shifted oscillator signal and the PPG signal;
   determining, using the patient monitor, the respiration rate based on the amplitude demodulated signal; and
   displaying, using a display, the respiration rate.

2. The method of claim 1, wherein the patient monitor is configured to receive the PPG signal from a pulse oximetry sensor, wherein the pulse oximetry sensor detects light attenuated by the subject.

3. The method of claim 1, wherein a product signal generated by multiplying the phase-shifted oscillator signal and the PPG signal is low pass filtered before generating the amplitude demodulated signal.

4. The method of claim 1, wherein determining the respiration rate comprises:
   generating an autocorrelation sequence based on the amplitude demodulated signal; and
   determining the respiration rate based on the autocorrelation sequence.

5. The method of claim 1, wherein the PPG signal is band pass filtered based on a heart rate associated with the PPG signal.

6. The method of claim 1, wherein the oscillator signal is generated using voltage controlled oscillator or a modulo-N counter.

7. The method of claim 1, wherein the modulo-N counter has a length controlled based on the phase difference between the PPG signal and the oscillator signal.

8. The method of claim 1, wherein the PPG signal comprises a fixed length analysis window.

9. The method of claim 1, wherein the oscillator signal is an approximation of the PPG signal.

10. The method of claim 1, wherein the phase-shifted oscillator signal matches phase and frequency of the PPG signal.

11. A patient monitor for determining respiration rate, the patient monitor comprising:
    an interface configured to receive a photoplethysmograph (PPG) signal;
    an oscillator configured to generate an oscillator signal;
    a processor configured to:
    generate a phase-shifted oscillator signal based on a phase difference between the PPG signal and the oscillator signal;
    generate an amplitude demodulated signal by multiplying the phase-shifted oscillator signal and the PPG signal; and
    determine respiration rate based on the amplitude demodulated signal; and
    a display configured to display the respiration information.

12. The patient monitor of claim 11, wherein the interface is configured to receive the PPG signal from a pulse oximetry sensor, wherein the pulse oximetry sensor detects light attenuated by the subject.

13. The patient monitor of claim 11, wherein a product signal generated by multiplying the phase-shifted oscillator signal and the PPG signal is low pass filtered before generating the amplitude demodulated signal.

14. The patient monitor of claim 11, wherein determining the respiration rate comprises:
    generating an autocorrelation sequence based on the amplitude demodulated signal; and
    determining the respiration rate based on the autocorrelation sequence.

15. The patient monitor of claim 11, wherein the processor is configured to band pass filter the PPG signal based on a heart rate associated with the PPG signal.

16. The patient monitor of claim 11, wherein the oscillator is configured to generate the oscillator signal using voltage controlled oscillator or a modulo-N counter.

17. The patient monitor of claim 11, wherein the modulo-N counter has a length controlled based on the phase difference between the PPG signal and the oscillator signal.

18. The patient monitor of claim 11, wherein the PPG signal comprises a fixed length analysis window.

19. The patient monitor of claim 11, wherein the oscillator signal is an approximation of the PPG signal.

20. The patient monitor of claim 11, wherein the phase-shifted oscillator signal matches phase and frequency of the PPG signal.

* * * * *